United States Patent
Tuck et al.

(12) 
(10) Patent No.: US 6,274,743 B1
(45) Date of Patent: *Aug. 14, 2001

(54) PROCESS FOR THE PREPARATION OF BUTANEDIOL, BUTYROLACTONE AND TETRAHYDROFURAN

(75) Inventors: Michael W. M. Tuck, London; Philip H. D. Eastland, Middlesex; Andrew G. Hiles, Buckinghamshire; Graham Reed, London, all of (GB)

(73) Assignee: BASF Aktiengesellschaft (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/555,015

(22) PCT Filed: Mar. 19, 1999

(86) PCT No.: PCT/GB99/00881

§ 371 Date: Jun. 29, 2000

§ 102(e) Date: Jun. 29, 2000

(87) PCT Pub. No.: WO99/48852

PCT Pub. Date: Sep. 30, 1999

(30) Foreign Application Priority Data

Mar. 23, 1998 (GB) ................................. 98302163

(51) Int. Cl.$^7$ ............................................. C07D 307/02
(52) U.S. Cl. ........................... 549/295; 549/325; 549/429
(58) Field of Search ................... 549/295, 429, 549/325

(56) References Cited

U.S. PATENT DOCUMENTS

| | | | |
|---|---|---|---|
| 2,638,481 | 5/1953 | Nachod, Jr. | 260/533 |
| 2,893,924 | 7/1959 | Courtier | 202/42 |
| 3,040,059 | 6/1962 | Hoyte | 260/346.4 |
| 3,818,680 | 6/1974 | Marquis | 55/48 |
| 3,850,758 | 11/1974 | Smith et al. | 203/38 |
| 3,891,680 | 6/1975 | Katsumoto et al. | 260/246.8 M |
| 4,071,540 | 1/1978 | Marquis | 260/346.76 |
| 4,118,403 | 10/1978 | White | 260/346.76 |
| 4,584,419 | 4/1986 | Sharif et al. | 568/864 |
| 4,751,334 | 6/1988 | Turner et al. | 29/136 |
| 4,767,869 | 8/1988 | Harrison et al. | 549/295 |
| 4,795,824 | 1/1989 | Kippax et al. | 560/204 |
| 4,919,765 | 4/1990 | Wilkes et al. | 203/64 |
| 4,945,173 | 7/1990 | Wood | 549/295 |
| 5,254,758 | 10/1993 | Hiles et al. | 568/881 |
| 5,310,954 | 5/1994 | Hiles et al. | 549/429 |
| 5,347,021 | 9/1994 | Taylor et al. | 549/325 |
| 6,077,964 | * 6/2000 | Tuck et al. | 549/295 |
| 6,100,410 | * 8/2000 | Tuck et al. | 549/325 |

FOREIGN PATENT DOCUMENTS

| | | | |
|---|---|---|---|
| 0 373 947 B1 | 9/1993 | (EP) | 31/20 |
| 1.125.014 | 4/1955 | (FR) . | |
| 2 285 386 | 4/1976 | (FR) | 307/60 |
| 727828 | 4/1955 | (GB) | 1/1 |
| 763339 | 12/1956 | (GB) | 1/1 |
| 768551 | 2/1957 | (GB) | 2/3 |
| 35-7460 | 1/1930 | (JP) . | |
| 32-8408 | 8/1930 | (JP) . | |

(List continued on next page.)

Primary Examiner—Johann Richter
Assistant Examiner—Elvis O. Price
(74) Attorney, Agent, or Firm—Nixon & Vanderhye P.C.

(57) ABSTRACT

Butane-1,4-diol, gamma-butyrolactone or tetrahydrofuran are prepared by vapor phase hydrogenation of a C4-dicarboxylic acid derivative. A maleic anhydride containing vapor stream is contacted in an absorption zone with a first high boiling solvent. A waste gas stream is passed to a scrubbing zone containing a second, higher boiling solvent. The waste gas is purged and the first and second solvents are recovered and recycled. Maleic anhydride is obtained from the absorption zone and converted to a maleic acid diester, which is stripped from the first solvent with hydrogen. The desired products are obtained by hydrogenation.

36 Claims, 2 Drawing Sheets

FOREIGN PATENT DOCUMENTS

| | | | |
|---|---|---|---|
| WO 86/03189 | 6/1986 | (WO) | 29/17 |
| WO 88/00937 | 2/1988 | (WO) | 29/136 |
| WO 90/03127 | 4/1990 | (WO) | 11/25 |
| WO 90/08127 | 7/1990 | (WO) | 67/8 |
| WO 91/01960 | 2/1991 | (WO) | 29/14 |
| WO 97/43234 | 11/1997 | (WO) | 29/149 |
| WO 97/43242 | 11/1997 | (WO) | 67/8 |

* cited by examiner

PROCESS FOR THE PREPARATION OF BUTANEDIOL, BUTYROLACTONE AND TETRAHYDROFURAN

This application is the National Stage of International application No. PCT/GB99/00881, filed Mar. 19, 1999.

This invention relates to the production of butane-1,4-diol, γ-butyrolactone and tetrahydrofuran.

Butane-1,4-diol, together with variable amounts of γ-butyrolactone and tetrahydrofuran, can be produced by hydrogenolysis of diesters of maleic acid, fumaric acid and mixtures thereof, or by hydrogenolysis of maleic anhydride. A major use of butane-1,4-diol is as a feedstock for the plastics industry, particularly for the production of polybutylene terephthalate. It is also used as an intermediate for the production of γ-butyrolactone and of the important solvent, tetrahydrofuran.

Maleic anhydride is normally produced by vapour phase oxidation of a hydrocarbon feedstock, such as benzene, mixed $C_4$ olefins, or n-butane, in the presence of a partial oxidation catalyst. In the partial oxidation of benzene there is typically used a supported vanadium pentoxide catalyst promoted with $MoO_3$ and possibly other promoters. The reaction temperature is from about 400° C. to about 455° C. and the reaction pressure is from about 1 bar to about 3 bar, while about 4 times the theoretical amount of air is used in order to stay outside the explosive limits. The contact time is about 0.1 s. When the feedstock is a mixed $C_4$ olefin feedstock, i.e. a mixed butenes feedstock, then the partial oxidation catalyst may be vanadium pentoxide supported on alumina. Typical reaction conditions include use of a temperature of from about 425° C. to about 485° C. and a pressure of from about 1.70 bar to about 2.05 bar. The volume ratio of air to butenes may be about 75:1 in order to stay below explosive limits. Alternatively it is possible, according to more modern practice, to design the plant so that satisfactory safe operation can be achieved, despite the fact that the feed mixture of air and butenes is within the flammable limits. In the case of 1-butane as feedstock, the catalyst is typically vanadium pentoxide and the reaction conditions include use of a temperature of from about 350° C. to about 450° C. and a pressure of from about 1 bar to about 3 bar. The air:n-butane volume ratio may be about 20:1, even though this may be within the flammable limits. One design of reactor for such partial oxidation reactions comprises vertical tubes surrounded by a jacket through which a molten salt is circulated in order to control the reaction temperature.

In each case a hot vaporous reaction mixture is recovered from the exit end of the reactor which comprises maleic anhydride vapour, water vapour, carbon oxides, oxygen, nitrogen, and other inert gases, besides organic impurities such as formic acid, acetic acid, acrylic acid, and unconverted hydrocarbon feedstock.

One way of recovering maleic anhydride from such a reaction mixture is to cool it to about 150° C. using a steam-producing stream and then to cool it further to about 60° C. by cooling it against water in order to condense part of the maleic anhydride, typically about 30% to about 60% of the maleic anhydride present. The remainder of the stream is then scrubbed with water.

Scrubbing with water or with an aqueous solution or slurry is described, for example, in U.S. Pat. No. 2,638,481. Such scrubbing results in production of a solution of maleic acid which is then dehydrated, by distilling with xylene, for example, so as to remove the water and re-form the anhydride. A disadvantage of such a procedure, however, is that an unacceptable proportion of the product remains in the vapour phase. In addition, some of the maleic acid is inevitably isomerised to fumaric acid. The byproduct fumaric acid represents a loss of valuable maleic anhydride and is difficult to recover from the process system since it tends to form crystalline masses which give rise to process problems.

Because of this isomerisation problem a variety of other anhydrous scrubbing liquids have been proposed. For example, dibutyl phthalate has been proposed as scrubbing liquid in GB-A-727828, GB-A-763339, and GB-A-768551. Use of dibutyl phthalate containing up to 10 weight % phthalic anhydride is suggested in U.S. Pat. No. 4,118,403. U.S. Pat. No. 3,818,680 teaches use of a normally liquid intramolecular carboxylic acid anhydride, such as a branched chain $C_{12-15}$-alkenyl substituted succinic anhydride, for absorption of maleic anhydride from the reaction mixture exiting the partial oxidation reactor. Tricresyl phosphate has been proposed for this purpose in FR-A-1125014. Dimethyl terephthalate is suggested for this duty in JP-A-32-8408 and dibutyl maleate in JP-A-35-7460. A high molecular weight wax as scrubbing solvent is taught in U.S. Pat. No. 3,040,059, while U.S. Pat. No. 2,893,924 proposes scrubbing with diphenylpentachloride. Use of an aromatic hydrocarbon solvent having a molecular weight between 150 and 400 and a boiling point above 140° C. at a temperature above the dew point of water in the vaporous reaction mixture, for example dibenzylbenzene, is suggested in FR-A-2285386. Absorption of maleic anhydride from the vaporous partial oxidation reaction mixture in dimethylbenzophenone followed by distillation is described in U.S. Pat. No. 3,850,758. Polymethylbenzophenones, at least a portion of which contain at least 3 methyl groups, can be used as liquid absorbent for maleic anhydride according to U.S. Pat. No. 4,071,540. Dialkyl phthalate esters having $C_4$ to $C_8$ alkyl groups and a total of 10 to 14 carbon atoms in both alkyl groups are proposed for absorption of maleic anhydride from the reaction mixture in U.S. Pat. No. 3,891,680. An ester of a cycloaliphatic acid, for example dibutyl hexahydrophthalate, is suggested as absorption solvent for maleic anhydride in ZA-A-80/1247.

It has also been proposed to effect direct condensation of maleic anhydride from the reaction mixture exiting the partial oxidation reactor. However, this procedure is inefficient because an unacceptable proportion of the maleic anhydride remains in the vapour phase.

The maleic anhydride product recovered following condensation or by scrubbing or absorption and distillation can then be subjected to hydrogenation to yield butane-1,4-diol, together with variable amounts of γ-butyrolactone and tetrahydrofuran, as described in U.S. Pat. No. 5,347,021 and EP-B-0373947 the disclosure of which is herein incorporated by reference.

Alternatively the recovered maleic anhydride can then be reacted with a suitable $C_1$ to $C_4$ alkanol, such as methanol or ethanol, to yield the corresponding di-($C_1$ to $C_4$ alkyl) maleate. This di-($C_1$ to $C_4$ alkyl) maleate may contain a minor amount of the corresponding di-($C_1$ to $C_4$ alkyl) fumarate, besides traces of the corresponding mono-($C_1$ to $C_4$ alkyl) maleate and/or fumarate. The di-($C_1$ to $C_4$ alkyl) maleate can then be subjected to hydrogenolysis to yield a mixture of butane-1,4-diol, together with variable amounts of γ-butyrolactone and tetrahydrofuran, depending upon the hydrogenolysis conditions that are selected, and of the $C_1$ to $C_4$ alkanol which can be recycled to produce further di-($C_1$ to $C_4$ alkyl) maleate.

Processes and plant for the production of dialkyl maleates from maleic anhydride are described, for example, in U.S. Pat. No. 4,795,824 and in WO-A-90/08127. This last mentioned document describes a column reactor containing a plurality of esterification trays each having a predetermined liquid hold-up and containing a charge of a solid esterification catalyst, such as an ion exchange resin containing pendant sulphonic acid groups. A liquid phase containing, for example, a carboxylic acid component flows down the column from one esterification tray to the next lower one against an upflowing stream of vapour of the lower boiling component of the esterification reagents, typically the $C_1$ to $C_4$ alkanol. Water of esterification is removed from the top of the column reactor in a vapour stream, while ester product is recovered from the sump of the reactor. As the liquid flows down the trays it encounters progressively drier reaction conditions and the esterification reaction is driven further towards 100% ester formation. This column reactor may be followed by a polishing reactor operating under liquid phase reaction conditions, the ester-containing stream from the bottom of the column reactor being admixed with further $C_1$ to $C_4$ alkanol prior to admission to the polishing reactor. When used for the production of a di-($C_1$ to $C_4$ alkyl) maleate, the column reactor can be preceded by a non-catalytic monoesterification reactor in which maleic anhydride is reacted with the $C_1$ to $C_4$ alkanol in the absence of an added catalyst to form the mono-($C_1$ to $C_4$ alkyl) maleate.

The hydrogenation of dialkyl maleates to yield butane-1,4-diol is discussed further in U.S. Pat. No. 4,584,419, U.S. Pat. No. 4,751,334, and WO-A-88/00937, the disclosures of all of which are herein incorporated by reference.

In WO-A-97/43242 a process is described in which maleic anhydride is absorbed in a high boiling solvent having a boiling point that is at least 30° C. higher than that of maleic anhydride at atmospheric pressure, for example dimethyl phthalate. Then the maleic anhydride in the resulting solution is esterified to form the corresponding di-($C_1$ to $C_4$ alkyl) maleate, which is subsequently stripped from the solution using a hydrogen-containing gas stream to yield a vaporous mixture which is then subjected to vapour phase hydrogenation. A similar procedure in which the esterification step is omitted and the maleic anhydride is stripped from the solution in the high boiling solvent and subjected to vapour phase hydrogenation is described in WO-A-97/43234.

It would be desirable to improve the production of butane-1,4,-diol, γ-butyrolactone and tetrahydrofuran, from maleic anhydride by hydrogenation. In particular it would be desirable to reduce the capital cost of construction of such a plant and also to reduce its running costs, thereby making butane-1,4-diol, γ-butyrolactone and tetrahydrofuran more readily available.

It would also be desirable to simplify the production of butane-1,4,-diol, γ-butyrolactone and tetrahydrofuran, from maleic anhydride by the di-($C_1$ to $C_4$ alkyl) maleate hydrogenolysis route. In particular it would be desirable to reduce the capital cost of construction of such a plant and also to reduce its running costs, thereby making butane-1,4-diol, γ-butyrolactone and tetrahydrofuran more readily available.

It is accordingly an object of the present invention to improve the production of butane-1,4,-diol, γ-butyrolactone and tetrahydrofuran from maleic anhydride. It is also an object of the present invention to simplify the production of butane-1,4,-diol, γ-butyrolactone and tetrahydrofuran from maleic anhydride by the di-($C_1$ to $C_4$ alkyl) maleate hydrogenolysis route. A further object is to reduce the capital cost of construction of such a plant by reducing significantly the numbers of distillation columns and the amount of other equipment required. It further seeks to reduce the running costs of a butane-1,4-diol production plant, thereby making butane-1,4-diol, γ-butyrolactone and tetrahydrofuran more readily available.

According to the present invention there is provided a process for the production of at least one $C_4$ compound selected from butane-1,4-diol, γ-butyrolactone and tetrahydrofuran, which includes the step of hydrogenation in the vapour phase of a $C_4$ dicarboxylic acid derivative in the presence of a heterogeneous hydrogenation catalyst, said $C_4$ dicarboxylic acid derivative being selected from maleic anhydride and di-($C_1$ to $C_4$ alkyl) esters of a $C_1$ to $C_4$ dicarboxylic acid, which process comprises:

(a) contacting a vaporous stream containing maleic anhydride vapour, water vapour, and carbon oxides in an absorption zone with a first high boiling organic solvent having a boiling point at atmospheric pressure which is at least is about 30° C. higher than that of the $C_4$ dicarboxylic acid derivative thereby to form a solution of maleic anhydride in the first high boiling organic solvent;

(b) recovering from the absorption zone a waste gas stream containing a minor amount of said first high boiling organic solvent;

(c) contacting the waste gas stream of step (b) in a scrubbing zone with a second high boiling organic solvent having a boiling point at atmospheric pressure which is at least 30° C. higher than that of the first high boiling organic solvent, thereby to form a solution of the first high boiling organic solvent in the second high boiling organic solvent and to yield a washed waste gas;

(d) recovering first high boiling solvent from the solution of step (c) for recycle to step (a);

(e) recycling residual second high boiling solvent from step (d) to step (b);

(f) purging washed waste gas of step (c);

(g) converting maleic anhydride in said solution of step (a), if necessary, to said $C_4$ dicarboxylic derivative;

(h) contacting the solution of said $C_4$ dicarboxylic acid derivative in the first high boiling solvent with a gaseous stream containing hydrogen thereby to strip said $C_4$ dicarboxylic acid derivative therefrom and to form a vaporous stream comprising hydrogen and said $C_4$ dicarboxylic acid derivative;

(i) contacting material of the vaporous stream of step (h) in a hydrogenation zone under hydrogenation conditions with a heterogeneous hydrogenation catalyst thereby to convert said $C_4$ dicarboxylic acid derivative to at least one $C_4$ compound selected from butane-1,4-diol, γ-butyrolactone and tetrahydrofuran; and (j) recovering from the hydrogenation zone a product stream containing said at least one $C_4$ compound.

In the process of the invention step (g) is optional; thus the $C_4$ dicarboxylic acid derivative that is subjected to hydrogenation in step (i) can be maleic anhydride or it can be a di-($C_1$ to $C_4$ alkyl) maleate, fumarate or a mixture of di-($C_1$ to $C_4$ alkyl) maleate, succinate and/or fumarate.

The vaporous stream of step (a) of the process of the invention is preferably produced by partial oxidation of a hydrocarbon feedstock in the presence of a partial oxidation catalyst using molecular oxygen, typically in the form of air. The hydrocarbon feedstock can be benzene, or a mixed $C_4$ olefin stream, but is most preferably U-butane. The use of n-butane as hydrocarbon feedstock is currently preferred upon the grounds of cost since it is a cheaper feedstock than benzene or butenes. Hence in the process of the invention the feedstock used for production of the maleic anhydride containing vaporous stream of step (a) is most preferably n-butane and the catalyst is preferably vanadium pentoxide. Typical partial oxidation conditions in this case include use of a temperature of from about 350° C. to about 450° C. and a pressure of from about 1 bar to about 3 bar, an air to n-butane ratio of from about 15:1 to about 50:1, e.g. about 20:1 and a partial oxidation catalyst comprising vanadium pentoxide; the contact time is typically from about 0.01 s to about 0.5 s, e.g. about 0.1 s.

Partial oxidation of the hydrocarbon feedstock is conveniently conducted in a reactor which comprises. vertical tubes surrounded by a jacket through which a molten salt is circulated in order to control the reaction temperature. The vaporous stream from the partial oxidation reactor can then be cooled by external cooling with boiler feed water to raise steam, and possibly also by further external cooling with cooling water to a temperature in the range of from about 60° C. to about 160° C.

In step (a) of the process of the invention the vaporous maleic anhydride stream is preferably contacted with the first high boiling solvent at a temperature in the range of from about 60° C. to about 160° C., preferably from about 80° C. to about 120° C., and at a pressure of from about 1 bar to about 3 bar so as to form a solution comprising maleic anhydride in the first high boiling solvent. The contacting can be carried out by bubbling the vaporous stream through a body of the first high boiling solvent. Alternatively the first high boiling solvent can be sprayed into the vaporous stream. Countercurrent contacting devices can also be employed wherein the ascending vaporous stream is contacted by a descending stream of first high boiling solvent in a gas-liquid contacting device, such as a packed scrubber tower or a scrubber tower provided with trays. In this step the first high boiling solvent will typically be at a lower temperature than the vaporous stream so that the latter is cooled.

In the resulting solution of maleic anhydride in the first high boiling solvent the concentration of maleic anhydride may range from about 100 g/l to about 400 g/l.

The first high boiling solvent has a boiling point at atmospheric pressure that is at least about 30° C. higher, and preferably at least about 60° C. to about 70° C. higher, than that of the $C_4$ dicarboxylic acid derivative, i.e. maleic anhydride (if step (g) is omitted) or a di-($C_1$ to $C_4$ alkyl) maleate, fumarate or a mixture of a di-($C_1$ to $C_4$ alkyl) maleate, succinate and/or fumarate (if step (g) is included).

It is also the case that the second high boiling solvent has a boiling point at atmospheric pressure that is at least about 30° C. higher, and preferably at least about 50° C. to about 70° C. higher, than that of the first high boiling solvent.

As examples of suitable high boiling solvents from which the first and second solvents can be selected, there can be mentioned dibutyl phthalate; tricresyl phosphate; dibutyl maleate; a high molecular weight wax; an aromatic hydrocarbon solvent having a molecular weight between 150 and 400 and a boiling point above 140° C., such as dibenzylbenzene; and dialkyl phthalate esters having $C_4$ to $C_8$ alkyl groups and a total of 10 to 14 carbon atoms in both alkyl groups. Examples of esters which can be used as high boiling solvent include di-($C_1$ to $C_4$ alkyl) phthalates, such as dimethyl phthalate, diethyl phthalates, di-n- or -i-propyl phthalate, and dibutyl phthalate, di-($C_1$ to $C_4$ alkyl) esters, e.g. dimethyl esters, of other aromatic acids, such as dimethyl 2,3-naphthalene-dicarboxylate, diesters of cyclic laliphatic diacids, such as dimethyl 1,4-cyclohexane-dicarboxylate, and methyl esters of long chain fatty acids containing, for example, from 14 to 30 carbon atoms. Other solvents that can be used include high boiling ethers such as dialkyl ethers of polyethylene glycols of appropriate molecular weight, such as tetraethyleneglycol dimethyl or dibutyl ether.

The first and second high boiling solvents can alternatively be chosen from esters of alkyl dicarboxylic acids containing up to 13 carbon atoms, such as dimethyl, diethyl, di-n- or -iso-propyl, di-n-, -sec-, or iso-butyl esters of suberic acid, azelaic acid, sebacic acid, undecanedioic acid, dodecanedioic acid, and tridecanedioic acid. It is preferred that the alkyl moiety in such an ester shall be derived from the same alkanol as the $C_1$ to $C_4$ alkanol used in the esterification step (g), if the process includes this step. In this way any transesterification reactions that may occur do not give rise to additional esters. Thus when the alkanol used is methanol and the dialkyl maleate is dimethyl maleate, any ester used as the first high boiling solvent is preferably also a dimethyl ester, such as dimethyl sebacate.

The first and second high boiling solvents may alternatively be selected from mono- and di-($C_{10}$ to $C_{18}$ alkyl) esters of one of the $C_4$ alkyl dicarboxylic acids, i.e. maleic acid, fumaric acid, and succinic acid, and mixtures thereof. Examples of such esters include the esters and mixtures thereof derived from n-decyl alcohol, lauryl alcohol, myristyl alcohol, cetyl alcohol, stearyl alcohol, and eicosanol. In this case some hydrolysis of the high boiling ester may occur in the esterification zone, if an esterification step (g) is included in the process of the invention, resulting in liberation of a minor proportion of the corresponding $C_{10}$ to $C_{18}$ alkyl alcohol. In addition some transesterification may occur in the esterification zone resulting in formation of a minor amount of a mono-($C_1$ to $C_4$ alkyl) mono-($C_{10}$ to $C_{18}$ alkyl) ester of the $C_4$ alkyl dicarboxylic acid. For example, if dilauryl maleate is used as the high boiling ester and if methanol is used as the $C_1$ to $C_4$ alkanol, then a minor amount of methyl lauryl maleate can be formed by transesterification. However, the formation of these minor byproducts is not disadvantageous because any free $C_{10}$ to $C_{18}$ alkanol can react with fresh maleic anhydride in step (a) to form fresh mono- or di-($C_{10}$ to $C_{18}$ alkyl) maleate. In addition any mono-($C_1$ to $C_4$ alkyl) mono-($C_{10}$ to $C_{18}$ alkyl) ester of the $C_4$ alkyl dicarboxylic acid can undergo transesterification on the next occasion that it passes through the esterification zone to form the desired solvent or the desired di-($C_1$ to $C_4$ alkyl) maleate.

The first and second high boiling solvents may alternatively be selected from ($C_1$ to $C_4$ alkyl) esters of naphthalenemonocarboxylic acids, such as methyl naphthalene-2-carboxylate, from tri-($C_1$ to $C_4$ alkyl) esters of aromatic tricarboxylic acids, such as trimethyl benzene-1,2,4-tricarboxylate, or from di-($C_1$ to $C_4$ alkyl) esters of isophthalic acid, such as dimethyl isophthalate.

When an ester is used as the first high boiling solvent it is preferred that its alkyl moiety or moieties shall be derived from the same alkanol as any $C_1$ to $C_4$ alkanol used in step. (g). In this way any transesterification reactions that may occur do not give rise to additional esters. Thus when the alkanol used is methanol and the dialkyl maleate is dimethyl maleate, any ester used as the first high boiling solvent is preferably also a dimethyl ester, such as dimethyl sebacate.

The first high boiling solvent used in step (a) conveniently comprises material resulting from the hydrogen stripping step (h). Hence it may contain already some $C_4$ dicarboxylic acid derivative, e.g. maleic anhydride or di-($C_1$ to $C_4$ alkyl) maleate.

If the first high boiling solvent is a methyl ester, then it will often be convenient to use the corresponding butyl ester as the second high boiling solvent. For example, if the first high boiling solvent is dimethyl phthalate, then the second high boiling solvent may be di-n-butyl phthalate.

In step (d) of the process of the invention recovery of first high boiling solvent from the solution of step (c) can be carried out by stripping with air or other inert non-condensable gas. In this case the air or other non-condensable gas stream, after subjection to condensation conditions in order to effect condensation of second high boiling solvent therefrom, can be supplied to the base of the absorption zone of step (a). Alternatively recovery of first high boiling solvent from the solution of step (c) can be carried out by distillation.

Esterification of the maleic anhydride with the $C_1$ to $C_4$ alkanol can be effected in step (g) in an esterification zone. This may comprise a non-catalytic reactor in which the maleic anhydride in the solution in the high boiling ester undergoes reaction in the absence of added catalyst with the $C_1$ to $C_4$ alkanol to form the corresponding mono-($C_1$ to $C_4$ alkyl) maleate. The reaction is:

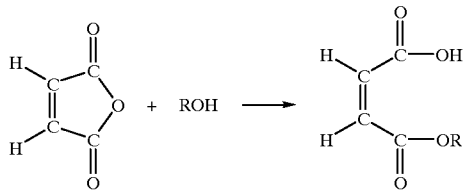

where R is a $C_1$ to $C_4$ alkyl radical. Some conversion of the mono-($C_1$ to $C_4$ alkyl) maleate to the corresponding di-($C_1$ to $C_4$ alkyl) maleate may also occur. The reaction concerned is:

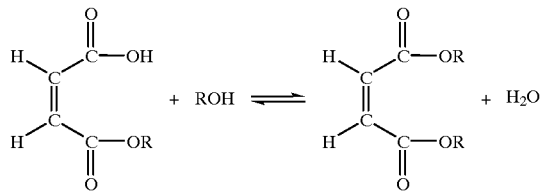

where R is as defined above.

Such a non-catalytic reactor can be operated under monoesterification conditions which typically comprise use of a temperature of from about 65° C. to about 260° C. and a pressure of from about 1 bar to about 50 bar. This can be followed by a catalytic esterification stage. For example, the catalytic esterification stage may comprise a plurality of stirred tank reactors such as is disclosed in U.S. Pat. No. 4,795,824. Preferably, however, the catalytic esterification stage comprises a column reactor of the type disclosed in WO-A-90/03127. In this case the non-catalytic monoesterification stage may comprise a stirred tank reactor or a column reactor containing one or more trays which do not contain any esterification catalyst and which is fed from the bottom with methanol or other $C_1$ to $C_4$ alkanol vapour, while the maleic anhydride solution from step (a) is fed downward through the column reactor.

If the catalytic esterification stage comprises a column reactor of the type disclosed in WO-A-90/03127, then the solution of maleic anhydride (or a solution comprising the corresponding mono-($C_1$ to $C_4$ alkyl) maleate, if a separate monoesterification stage is used) in the high boiling ester is fed to the top esterification tray of the column reactor, while an excess of $C_1$ to $C_4$ alkanol vapour is fed to the bottom of the reactor.

In the column reactor the esterification trays each hold a charge of a solid esterification catalyst. Each tray has a vapour upcomer means to permit vapour to enter the tray from below and to agitate the mixture of liquid and solid esterification catalyst in a zone of turbulence on the tray and to keep the catalyst particles in suspension. In order avoid the danger of "hot spots" forming on the tray through formation of pockets of settled catalyst particles, the floor of each tray is preferably designed so as to slope towards the zone of turbulence at a slope which exceeds the angle of repose of the catalyst particles under the liquid. In a addition each esterification tray has a downcomer means which permits liquid, but not catalyst particles, to flow down from that tray to the next lower one. Such a downcomer means will is usually be provided with a screen to prevent catalyst particles passing downwardly therethrough.

Typical reaction conditions in the column reactor include use of a temperature and pressure under which the $C_1$ to $C_4$ alkanol distils. Such temperature and pressure conditions will vary in dependence upon the $C_1$ to $C_4$ alkanol selected but will typically include use of a temperature of from about 65° C. to about 135° C. and a pressure of from about 1 bar to about 3 bar. A typical solid esterification catalyst is the ion exchange resin sold under the designation Amberlyst™ 16 by Rohm and Haas (U.K.) Limited of Lennig House, 2 Mason's Avenue, Crcydon CR9 3NB, England or that available as DPT1 ion exchange resin from Kvaerner Process Technology Limited of 20 Eastbourne Terrace, London W2 6LE, England.

In passing up the column from one esterification tray to the next higher one, the upflowing $C_1$ to $C_4$ alkanol vapour carries with it water of esterification. Thus the di-($C_1$ to $C_4$ alkyl) maleate-containing liquid passing down the column reactor from one esterification tray to the next lower one encounters drier and drier conditions as it proceeds down the column. In this way the esterification reaction leading to formation of the di-($C_1$ to $C_4$ alkyl) maleate is driven further and further towards 100% conversion to the di-($C_1$ to $C_4$ alkyl) maleate.

Any byproduct acid, such as acetic acid or acrylic acid, that is also present in the vaporous stream from the partial oxidation reactor, together with any maleic acid or fumaric acid present in the solution supplied to the esterification zone, will undergo conversion to the corresponding $C_1$ to $C_4$ alkyl ester or diester, as the case may be.

The vapour phase stream emerging from the topmost esterification tray comprises $C_1$ to $C_4$ alkanol vapour and water vapour; it may further include traces of minor byproducts such as the di-($C_1$ to $C_4$ alkyl) ether, besides traces of the di-($C_1$ to $C_4$ alkyl) maleate and of the $C_1$ to $C_4$ alkyl acrylate. A further additional tray or trays may be provided above the uppermost esterification tray to act as a form of washing column in order to return di-($C_1$ to $C_4$ alkyl) maleate to the esterification trays. The resulting vapour stream, which is now essentially free from di-($C_1$ to $C_4$ alkyl) maleate, exits the top of the column.

From the bottom of the column reactor there is recovered a liquid stream comprising a solution of the di-($C_1$ to $C_4$ alkyl) maleate in the high boiling ester. This is essentially acid free. If desired this liquid can be admixed with additional $C_1$ to $C_4$ alkanol and passed through a polishing reactor containing a bed of solid esterification catalyst operating under liquid phase operating conditions. Such conditions typically include use of a temperature of from about 65° C. to about 135° C. and a pressure of from about 1 bar to about 3 bar. A typical solid esterification catalyst is the ion exchange resin sold under the designation Amberlyst™ 16 by Rohm and Haas (U.K.) Limited of Lennig House, 2 Mason's Avenue, Croydon CR9 3NB, England or that available as DPT1 ion exchange resin from Kvaerner Process Technology Limited of 20 Eastbourne Terrace, London W2 6LE, England.

In step (h) of the process of the invention, a gas stream comprising hydrogen is passed through the solution of the $C_4$ dicarboxylic acid derivative.

The hydrogen stripping step is preferably conducted substantially at or at a pressure slightly higher than the inlet pressure to the ester hydrogenation zone. The hydrogen stripping step is similarly preferably conducted at substantially the desired inlet temperature to the hydrogenation step or a little below this temperature, for example from about 5° C. to about 20° C. below this temperature. Then the temperature can be raised to the desired inlet temperature by admixture of further hot hydrogen-containing gas which has the additional benefit of diluting the vaporous ester-containing stream and thereby ensuring that it is at a temperature above its dew point, preferably at least about 5° C. higher than its dew point.

When the $C_4$ dicarboxylic acid derivative is maleic anhydride, the hydrogenation step is advantageously conducted in the vapour phase, using a heterogeneous hydrogenation catalyst. Typical hydrogenation catalysts include promoted copper-based catalysts, such as a Cu/zn/Mg/Cr catalyst of the type described in J. Org. Chem 1, pages 177 to 185.

When the $C_4$ dicarboxylic acid derivative is a di-($C_1$ to $C_4$ alkyl) maleate, fumarate, or mixture thereof, hydrogenation is conducted at an elevated temperature of, for example, from about 150° C. to about 300° C., more usually from about 180° C. to about 280° C., and at a pressure of from about 5 bar to about 100 bar, preferably from about 10 bar to about 70 bar. In this case the hydrogenation step is advantageously conducted in the vapour phase, using a heterogeneous ester hydrogenation catalyst. Typical ester hydrogenation catalysts include reduced promoted copper catalysts, for example reduced copper chromite catalysts such as that sold under the designation PG 85/1 by Kvaerner Process Technology Limited of 20 Eastbourne Terrace, London W2 6LE.

The catalyst particles preferably have a particle size in the range of from about 0.5 mm to about 5 mm. The particles may be of any convenient shape, e.g. spheres, pellets, rings or saddles. When using a fixed bed of catalyst the reactor can be a shell-and-tube reactor, which can be operated substantially isothermally; however, it is preferably an adiabatic reactor. The use of an adiabatic reactor is advantageous since its capital cost is much lower than that of a shell-and-tube reactor and it is generally much easier to charge the reactor with the chosen catalyst.

From the hydrogenation zone there is recovered a hydrogenation product mixture which contains, in addition to the $C_1$ to $C_4$ alkanol, also butane-1,4-diol, and some tetrahydrofuran and γ-butyrolactone. Even if the primary product of interest is butane-1,4-diol, the presence of these minor amounts of tetrahydrofuran and γ-butyrolactone is not disadvantageous since these compounds are important chemicals of commerce and it is accordingly economic to recover them in pure form. If desired, γ-butyrolactone can be recycled to the hydrogenation zone to produce additional butane-1,4-diol. In addition the hydrogenolysis product mixture will normally contain minor amounts of the corresponding di-($C_1$ to $C_4$ alkyl) succinate, n-butanol, the corresponding dialkyl alkoxysuccinate, e.g. dimethyl methoxysuccinate if the $C_1$ to $C_4$ alkanol is methanol, and water.

For further details regarding vapour phase hydrogenation of maleic anhydride reference may be made to a paper by G. L. Castiglioni et al in Erdöl und Kohle-Erdgas-Petrochemie vereinigt mit Brennstoff-Chemie, Bd. 48, Heft 4/5, April/May 1995 at pages 174 to 178 under the heading Wissenschaft & Technik (Science & Technology).

For further details regarding hydrogenation of a di-($C_1$ to $C_4$ alkyl) maleate reference may be made to U.S. Pat. No. 4,584,419, WO-A-86/03189, WO-A-88/0937, U.S. Pat. No. 4,767,869, U.S. Pat. No. 4,945,173, U.S. Pat. No. 4,919,765, U.S. Pat. No. 5,254,758, U.S. Pat. No. 5,310,954, and WO-A-91/01960.

Teaching regarding subsequent purification of the crude hydrogenation product mixture, whether produced by hydrogenation of maleic anhydride or of a di-($C_1$ to $C_4$ alkyl) maleate can also be found in U.S. Pat. No. 4,584,419, WO-A-86/03189, WO-A-88/0937, U.S. Pat. No. 4,767,869, U.S. Pat. No. 4,945,173, U.S. Pat. No. 4,9197,65, U.S. Pat. No. 5,254,758, U.S. Pat. No. 5,310,954, and WO-A-91/01960. In a particularly preferred process the hydrogenation product mixture is purified by distillation in one or more stages, including distillation in a "light ends" column to separate overhead the volatile components of the mixture including tetrahydrofuran, and U-butanol. The bottoms product from the "light ends" column can then be further purified by distillation in one or more stages to yield pure butane-1,4-diol.

DETAILED DESCRIPTION OF THE PREFERRED EMBODIMENTS

Figure 1:
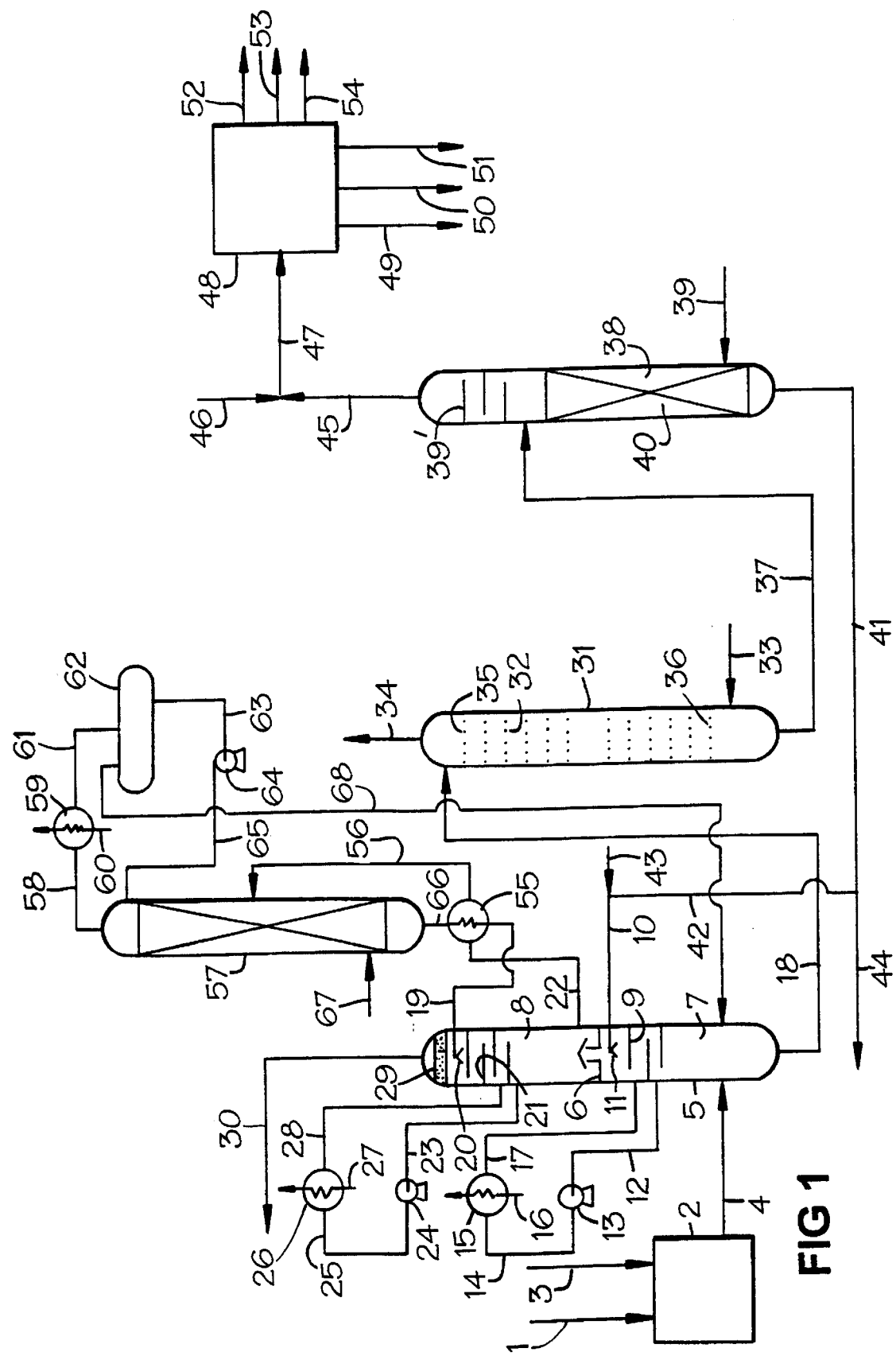
FIGS. 1 and 2 schematically depict plants for the production of butane-1,4-diol as well as some gamma-butyrolactone and tetrahydrofuran, by the hydrogenation of dimethyl maleate and maleic anhydride, respectively.

In order that the invention may be clearly understood and readily carried into effect two plants for the production of butane-1,4-diol, as well as some γ-butyrolactone and tetrahydrofuran, using a preferred process in accordance with the present invention will now be described, by way of example only, with reference to the accompanying drawings, FIGS. 1 and 2 of which are each a flow diagram of the respective plant.

It will be appreciated by those skilled in the art that, since the accompanying drawings are diagrammatic, many other items of equipment which are not shown in the drawings would be required in an actual plant. Such additional items of equipment are conventional in nature and include (but are not limited to) pumps, holding tanks, valves, pressure sensors, temperature sensors, pressure controllers, temperature controllers, level sensors, heaters, coolers, surge tanks, condensers, column reboilers, and the like. Any such additional items of equipment would be installed in accordance with conventional engineering practice and form no part of the present invention.

Referring to FIG. 1 of the drawings, the plant is designed to produce butane-1,4-diol, as well as γ-butyrolactone and tetrahydrofuran, by hydrogenation of dimethyl maleate. In this plant U-butane is supplied in line 1 at a pressure of from 1 to 3 bar and at a temperature of 400° C. to a partial oxidation plant 2 which is also supplied with air in line 3. Partial oxidation plant 2 is of conventional design and includes a partial oxidation reactor comprising tubes packed with a partial oxidation catalyst consisting of vanadium pentoxide and provided with a jacket through which molten salt can be circulated for the purpose of temperature control. The partial oxidation reactor is operated at an air:n-butane feed ratio of 20:1.

A hot vaporous partial oxidation product stream is cooled by external cooling against boiler feed water to raise steam and then against cooling water to reduce its temperature to 138° C. It is recovered from plant 2 in line 4. This contains 2.9% w/w maleic anhydride, 5.8% w/w water, 1.3% w/w carbon dioxide, 1.0% w/w carbon monoxide, 0.01% w/w acetic acid, 0.01% w/w acrylic acid, 15.7% w/w oxygen, and the balance essentially comprising nitrogen and other inert gases. It is supplied as a vaporous feed stream to the bottom of a column 5 which is divided by a bubble cap plate 6 into a bottom section 7 and a top section 8.

Lower section 7 of column 5 is provided with a number of washing trays 9. The vaporous feed stream passes up the lower section 7 against a downflowing spray of dimethyl phthalate which is supplied at a temperature of about 68° C. from line 10 via spray nozzles 11. A side stream of liquid is drawn off one of the lower trays 9 in line 12 and is pumped by pump 13 through line 14 to a heat exchanger 15 in which it is cooled by means of water supplied in line 16. The cooled liquid is returned to a higher tray 9 of lower section 7 by means of line 17.

From the bottom of the lower section 7 of column 5 there is recovered a liquid stream in line 18 which comprises a solution of approximately 22% w/w maleic anhydride and 0.04% w/w acrylic acid in dimethyl phthalate.

The off gas from the lower section 7 of column 5 passes up through bubble cap plate 6 into the top section 8 of column 5. Since this off gas will contain some dimethyl phthalate vapour, a stream of di-n-butyl phthalate from line 19 is sprayed through nozzles 20 into an upper part of top section 8 in order to scrub dimethyl phthalate out of this off gas. Top section 8 is provided with a number of washing trays 21. A solution of dimethyl phthalate in di-n-butyl phthalate collects in the lower part of top section 8 and is drawn off therefrom in line 22. Part of the liquid flowing down top section 8 is withdrawn in line 23 and is pumped by pump 24 through line 25 to a heat exchanger 26 which is cooled by water supplied by way of line 27. The cooled liquid is returned to a higher part of top section 8 in line 28.

The scrubbed gas exits top section 8 of column 5 through mist eliminator 29 and is purged from the plant in line 30. It can be passed, for example, to a waste burner.

The solution of maleic anhydride in dimethyl phthalate in line 18 is supplied to the top of a column reactor 31 of the type described in WO-A-90/08127. This comprises a number of esterification trays 32 mounted one above the other, each containing a charge of a solid esterification catalyst, such as Amberlyst™ 16 resin or DPT1 ion exchange resin, and each having a vapour upcomer for upflowing vapour and a liquid downcomer to permit liquid to flow down the column from one esterification tray to the next lower one. Methanol vapour is supplied to the bottom of column reactor by way of line 33. Water of esterification is removed in the vapour stream exiting the column reactor in line 34. Column reactor 31 is operated at a temperature of from about 110° C. to about 125° C. and at a pressure of from about 1 bar to about 3 bar. The residence time in the column reactor 31 is about 3 hours. Normally the temperature on the top tray will be somewhat higher (e.g. about 125° C.) than that on the lowermost tray 36 (e.g. about 115° C.).

A solution containing about 250 g/l dimethyl maleate in dimethyl phthalate is withdrawn from the bottom of column reactor 31 in line 37 and pumped to near the top of a stripping column 38 which is operated at a temperature of 170° C. and a pressure of 885 psia (61.02 bar). Column 38 has a number of distillation trays above the point of injection of the dimethyl maleate solution into column 38 so as to reduce carryover of dimethyl phthalate in the overhead stream from column 38. The solution of dimethyl maleate in dimethyl phthalate flows down through packing 40 in stripping column 38 against an upflowing stream of hydrogen from line 34. The stripped dimethyl phthalate is recycled from the bottom of stripping column 38 by way of lines 41 and 42 and line 10 to the top of the lower section 7 of column 5. Fresh dimethyl phthalate solvent can be added by means of line 43 while a purge stream of the recycled solvent stream can be taken in line 44.

From the top of stripping column 38 there emerges in line 45 a near saturated vapour mixture stream comprising dimethyl maleate in hydrogen, with a hydrogen:dimethyl maleate molar ratio of about 320:1. This vapour mixture stream is at a temperature of from about 180° C. to about 195° C. and at a pressure of 62 bar. It is diluted with further hot hydrogen from line 46 at a temperature of from about 180° C. to about 195° C. to yield a vaporous stream with a hydrogen:dimethyl maleate molar ratio of about 350:1 and is at least about 5° C. above its dew point.

This vaporous mixture passes onwards in line 47 to hydrogenation plant 48 which includes an adiabatic reactor packed with a reduced copper-based catalyst, for example, a reduced copper chromite catalyst, and operated at an inlet temperature of 173° C., an inlet pressure of 885 psia (61.02 bar), and an exit temperature of 190° C. The dimethyl maleate feed rate corresponds to a liquid hourly space velocity of 0.5 $h^{-1}$. The plant also includes a purification section in which the crude hydrogenation product mixture is distilled in several stages to yield pure butane-1,4-diol in line 49. Lines for separate recovery of γ-butyrolactone and tetrahydrofuran are indicated at 50 and 51 respectively. Other streams from hydrogenation plant 48 include a methanol stream 52, an n-butanol stream 53, and a "heavies" stream 54. Material from stream 52 can be recycled to line 33. n-butanol from stream 53 can be used to produce make-up di-n-butyl phthalate by, for example, ester interchange with dimethyl phthalate in the presence of a suitable ester interchange catalyst, such as titanium tetra-isopropoxide. Stream 54 will contain any high boiling hydrogenation product or byproduct, for example those resulting from hydrogenation of any traces of dimethyl phthalate present in the vapour mixture in line 45, e.g. 1,4-dihydroxymethylbenzene.

The solution of dimethyl phthalate in di-n-butyl phthalate in line 22 passes through heat exchanger 55 to line 56 and into an air stripper column 57. A vaporous stream comprising dimethyl phthalate is recovered overhead in line 58 and is passed through condenser 59, which is supplied with cooling water in line 60. The resulting condensate passes by way of line 61 into condensate drum 62. The condensate is recycled to the top of column 57 as a recycle stream through line 63 under the influence of pump 64 and through line 65.

From the bottom of distillation column 57 a stream of di-n-butyl phthalate is recovered in line 66 and is passed through heat exchanger 55 to line 19.

Air for stripping is supplied to the stripper column 57 in line 67. Line 68 conveys the air used for stripping (and hence laden with dimethyl phthalate vapour) from condensate drum 62 to the bottom part of lower section 7 of column 5.

If desired, a stream of nitrogen or other inert non-condensable gas (for example, the waste gas in line 30) can be used in place of air as the stripping gas supplied in line 67.

Instead of using dimethyl phthalate and di-n-butyl phthalate in the plant of FIG. 1, there can be used in place thereof any of the pairs of solvents listed below in Table 1.

TABLE 1

| First high boiling solvent | Second high boiling solvent |
| --- | --- |
| dimethyl dodecanedioate | di-n-butyl dodecanedioate |
| dimethyl sebacate | di-n-butyl sebacate |
| dimethyl isophthalate | di-n-butyl isophthalate |
| methyl stearate | n-butyl stearate |
| methyl linoleate | n-butyl linoleate |
| methyl oleate | n-butyl oleate |
| methyl naphthalene-2-carboxylate | n-butyl naphthalene-2-carboxylate |
| dimethyl naphthalene-2,6-dicarboxylate | di-n-butyl naphthalene-2,6-dicarboxylate |
| trimethyl benzene-1,2,4-tricarboxylate | tri-n-butyl benzene-1,2,4-tricarboxylate |
| dimethyl cyclohexane-1,4-dicarboxylate | di-n-butyl cyclohexane-1,4-dicarboxylate |
| dimethyl cyclohexane-1,2-dicarboxylate | di-n-butyl cyclohexane-1,2-dicarboxylate |

Figure 2:
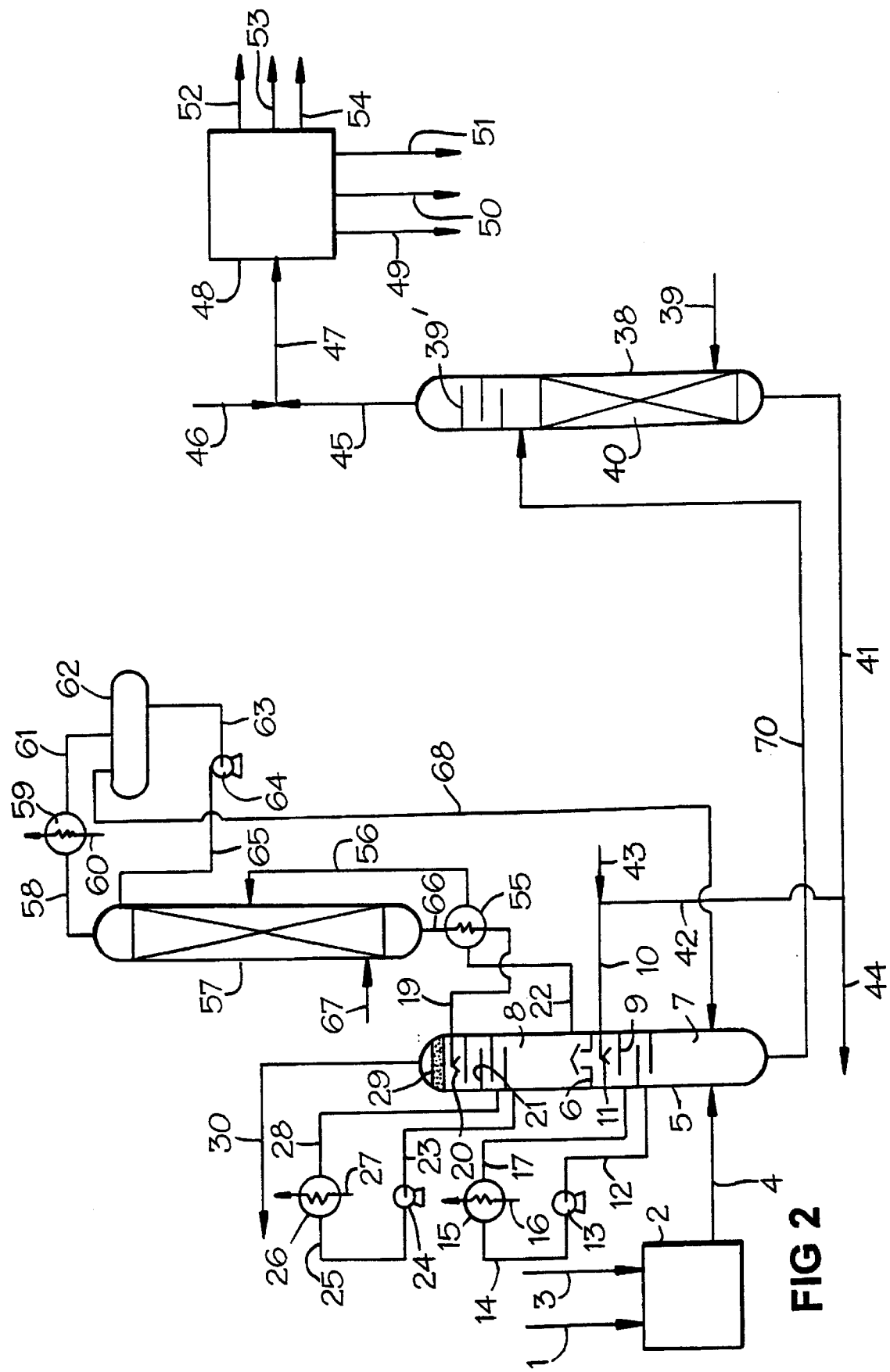

FIG. 2 illustrates a plant for the production of butane-1,4-diol, as well as some γ-butyrolactone and tetrahydrofuran, by hydrogenolysis of maleic anhydride. In this plant the same reference numerals are used to indicate like parts to those present in the plant of FIG. 1. Thus n-butane is supplied in line 1 at a pressure of from 1 to 3 bar and at a temperature of 400° C. to a conventional partial oxidation plant 2 which is also supplied with air in line 3. A vaporous partial oxidation product stream is recovered from plant 2 in line 4. It is fed to the lower section 7 of column 5, up which it passes against a downflowing spray of dimethyl dodecanedioate which is supplied at a temperature of about 68° C. from line 10. The operation of column 5 and of air stripper column 57 is essentially the same as described above in reference to the plant of FIG. 1. Moreover the liquid supplied by line 19 to the upper region of top section 8 of column 5 is di-n-butyl dodecanedioate.

From the bottom of column 5 there is recovered a liquid stream in line 70 which comprises a solution of approximately 15% w/w maleic anhydride and 0.04% w/w acrylic acid in dimethyl dodecanedioate. This is supplied to near the top of a stripping column 38 which is operated in a similar manner to column 38 of the plant of FIG. 1 at a temperature of 180° C. and a pressure of 580 psia (40 bar). Column 38 has a number of distillation trays 39 above the point of injection of the maleic anhydride solution from line 70 into column 38 so as to reduce carryover of dimethyl dodecanedioate in the overhead stream from column 38. The solution of maleic anhydride in dimethyl dodecanedioate flows down stripping column 38 against an upflowing stream of hydrogen from line 39. The stripped dimethyl dodecanedioate is recycled from the bottom of stripping column 38 by way of lines 41, 42 and 10 to the top of the lower section 7 of column 5. From the top of stripping column 38 there emerges in line 45 a near saturated vapour mixture stream comprising maleic anhydride in hydrogen, with a hydrogen:maleic anhydride molar ratio of about 400:1. This vapour mixture stream is at a temperature of from about 180° C. to about 200° C. and at a pressure of about 40 bar. It is diluted with further hot hydrogen from line 46 at a temperature of from about 180° C. to about 220° C. to yield a vaporous stream with a hydrogen:maleic anhydride molar ratio of about 450:1 and is at least about 5° C. above its dew point.

This vaporous mixture passes onwards in line 47 to hydrogenation plant 48 which includes an adiabatic reactor packed with a copper based catalyst (e.g. a promoted copper catalyst) and operated at an inlet temperature of 180° C., an inlet pressure of 565 psia (39 bar), and an exit temperature of 200° C. The maleic anhydride feed rate corresponds to a liquid hourly space velocity of 0.1 h⁻¹. The plant also includes a purification section in which the crude hydrogenation product mixture is distilled in several stages to yield pure butane-1,4-diol in line 49. Lines for separate recovery of γ-butyrolactone and tetrahydrofuran are indicated at 50 and 51 respectively.

The solvents dimethyl dodecanedioate and di-n-butyl dodecanedioate used in the plant of FIG. 2 can be replaced by any of the pairs of solvents listed in Table 1 above.

What is claimed is:

1. A process for the production of at least one $C_4$ compound selected from butane-1,4-diol, γ-butyrolactone and tetrahydrofuran, which includes the step of hydrogenation in the vapour phase of a $C_4$ dicarboxylic acid derivative in the presence of a heterogeneous hydrogenation catalyst, said $C_4$ dicarboxylic acid derivative being selected from maleic anhydride and di-($C_1$ to $C_4$ alkyl) esters of a $C_1$ to $C_4$ dicarboxylic acid, which process comprises:

(a) contacting a vaporous stream containing maleic anhydride vapour, water vapour, and carbon oxides in an absorption zone with a first high boiling solvent having a boiling point at atmospheric pressure which is at least about 30° C. higher than that of maleic anhydride thereby to form a solution of maleic anhydride in the first high boiling solvent;

(b) recovering from the absorption zone a waste gas stream containing a minor amount of said first high boiling solvent;

(c) contacting the waste gas stream of step (b) in a scrubbing zone with a second high boiling solvent having a boiling point at atmospheric pressure which is at least 30° C. higher than that of the first high boiling solvent, thereby to form a solution of the first high boiling solvent in the second high boiling solvent and to yield a washed waste gas;

(d) recovering first high boiling solvent from the solution of step (c) for recycle to step (a);

(e) recycling residual second high boiling solvent from step (d) to step (c);

(f) purging washed waste gas of step (c);

(g) converting maleic anhydride in said solution of step (a), if necessary, to said $C_4$ dicarboxylic derivative;

(h) contacting the solution of said $C_4$ dicarboxylic acid derivative in the first high boiling solvent with a gaseous stream containing hydrogen thereby to strip said $C_4$ dicarboxylic acid derivative therefrom and to form a vaporous stream comprising hydrogen and said $C_4$ dicarboxylic acid derivative;

(i) contacting material of the vaporous stream of step (h) in a hydrogenation zone under hydrogenation conditions with a heterogeneous hydrogenation catalyst thereby to convert said $C_4$ dicarboxylic acid derivative to at least one $C_4$ compound selected from butane-1,4-diol, γ-butyrolactone and tetrahydrofuran; and (j) recovering from the hydrogenation zone a product stream containing said at least one $C_4$ compound.

2. A process according to claim 1, in which the vaporous stream of step (a) is produced by partial oxidation of a hydrocarbon feedstock in the presence of a partial oxidation catalyst using molecular oxygen.

3. A process according to claim 2, in which the hydrocarbon feedstock is n-butane.

4. A process according to claim 3, in which the partial oxidation catalyst comprises vanadium pentoxide and in which the partial oxidation conditions include use of a temperature of from about 350° C. to about 450° C., a pressure of from about 1 bar to about 3 bar, an air to n-butane ratio of from about 15:1 to about 50:1 and a contact time of from about 0.01 s to about 0.5 s.

5. A process according to claim 1, in which in step (a) the vaporous maleic anhydride stream is contacted with the first high boiling solvent at a temperature in the range of from about 60° C. to about 160° C. and at a pressure of from about 1 bar to about 3 bar so as to form a solution comprising said $C_4$ dicarboxylic acid derivative in the first high boiling solvent.

6. A process according to claim 5, in which the contacting step is carried out in a countercurrent contacting device herein the ascending vaporous stream is contacted by a descending stream of first high boiling solvent in a gas-liquid contacting device.

7. A process according to claim 1, in which the first high boiling solvent is a methyl ester.

8. A process according to claim 7, in which the methyl ester is dimethyl phthalate.

9. A process according to claim 7, in which the methyl ester is a methyl ester or mixture of methyl esters of a long chain fatty acid or acids containing from 14 to 30 carbon atoms.

10. A process according to claim 7, in which the first high boiling solvent is dimethyl phthalene-2,6-dicarboxylate.

11. A process according to claim 7, in which the first high boiling solvent is trimethyl benzene-1,2,4-tricarboxylate.

12. A process according to claim 7, in which the second high boiling solvent is a butyl ester.

13. A process according to claim 12, in which the butyl ester is di-n-butyl phthalate.

14. A process according to claim 12, in which the butyl ester is a butyl ester or mixture of butyl esters of a long chain fatty acid or acids containing from 14 to 30 carbon atoms.

15. A process according to claim 12, in which the second high boiling solvent is di-n-butyl naphthalene-2,6-dicarboxylate.

16. A process according to claim 12, in which the second high boiling solvent is tri-n-butyl benzene-1,2,4-tricarboxylate.

17. A process according to claim 1, in which the hydrogen stripping step is conducted at substantially the inlet pressure to the hydrogenation zone.

18. A process according to claim 1, in which the hydrogen stripping step is conducted at a temperature in the range of from the inlet temperature to the hydrogenation zone to about 20° C. below the inlet temperature to the hydrogenation zone.

19. A process according to claim 1, in which the $C_4$ dicarboxylic acid derivative is maleic anhydride.

20. A process according to claim 19, in which the hydrogenation step is conducted in the vapour phase using a promoted copper catalyst at a temperature of from about 150° C. to about 300° C. and at a pressure of from about 5 bar to about 100 bar.

21. A process according to claim 1, in which the $C_4$ dicarboxylic acid derivative comprises a di-($C_1$ to $C_4$ alkyl) ester of maleic acid, fumaric acid or a mixture thereof.

22. A process according to claim 21, in which step (g) comprises the step of reacting maleic anhydride in the solution of maleic anhydride of step (a) under esterification conditions in an esterification zone with a $C_1$ to $C_4$ alkanol to form the corresponding di-($C_1$ to $C_4$ alkyl) maleate.

23. A process according to claim 22, in which the esterification zone comprises a non-catalytic reactor in which the maleic anhydride in the solution in the high boiling ester undergoes reaction in the absence of added catalyst with the $C_1$ to $C_4$ alkanol to form the corresponding mono-($C_1$ to $C_4$ alkyl) maleate.

24. A process according to claim 1, in which the catalytic esterification stage comprises a column reactor provided with a plurality of esterification trays each of which holds a charge of a solid esterification catalyst, has a vapour upcomer means to permit vapour to enter the tray from below and to agitate the mixture of liquid and solid esterification catalyst in a zone of turbulence on the tray and to keep the catalyst particles in suspension, and a downcomer means which permits liquid, but not catalyst particles, to flow down from that tray to the next lower one, the column reactor being supplied beneath the lowermost esterification tray with a stream of $C_1$ to $C_4$ alkanol vapour and to an upper esterification tray with a solution in the high boiling ester comprising a material selected from maleic anhydride, a mono-($C_1$ to $C_4$ alkyl) maleate wherein the $C_1$ to $C_4$ alkyl group is derived from the $C_1$ to $C_4$ alkanol, and a mixture thereof.

25. A process according to claim 24, in which the floor of each tray slopes towards the zone of turbulence at a slope which exceeds the angle of repose of the catalyst particles under the liquid.

26. A process according to claim 22, in a which the esterification zone comprises an autocatalytic esterification zone wherein the esterification conditions include use of a temperature of from about 70° C. to about 250° C., a pressure of from about 1 bar to about 50 bar and wherein maleic anhydride is converted by reaction with $C_1$ to $C_4$ alkanol at least in part to the corresponding mono-($C_1$ to $C_4$ alkyl) maleate.

27. A process according to claim 22, wherein the esterification zone includes a catalytic esterification zone wherein the esterification conditions include use of a temperature of from about 65° C. to about 135° C. and of a solid esterification catalyst comprising an ion exchange resin containing pendant sulphonic acid groups.

28. A process according to claim 22, in which the $C_1$ to $C_4$ alkanol is methanol and the di-($C_1$ to $C_4$ alkyl) maleate is dimethyl maleate.

29. A process according to claim 22, in which the first high boiling solvent is an alkyl ester whose alkyl moiety is derived from the same alkanol as the $C_1$ to $C_4$ alkanol used in the esterification step.

30. A process according to claim 22, in which the $C_1$ to $C_4$ alkanol is methanol, the di-($C_1$ to $C_4$ alkyl) maleate is dimethyl maleate, and the first high boiling solvent is also a methyl ester.

31. A process according to claim 22, in which the hydrogenation step is conducted in the vapour phase using a reduced promoted copper catalyst at a temperature of from about 150° C. to about 240° C. and at a pressure of from about 5 bar to about 100 bar.

32. A process according to claim 1, in which recovery of first high boiling solvent from the solution of step (c) includes stripping with air or other non-condensable gas.

33. A process according to claim 1, in which recovery of first high boiling solvent from the solution of step (c) is effected by distillation.

34. A process according to claim 1, in which there is recovered from the hydrogenation zone a hydrogenation product mixture which contains, in addition to butane-1,4-diol, also minor amounts of tetrahydrofuran and γ-butyrolactone.

35. A process according to claim 34, in which the hydrogenation product mixture is purified by distillation in one or more stages, including distillation in a "light ends" column to separate overhead the volatile components of the mixture including tetrahydrofuran, and n-butanol.

36. A process according to claim 35, in which the bottoms product from the "light ends" column is further purified by distillation in one or more stages to yield pure butane-1,4-diol.

* * * * *